(12) United States Patent
Atis

(10) Patent No.: US 8,715,634 B2
(45) Date of Patent: May 6, 2014

(54) VOLUMIZING COMPOSITIONS

(75) Inventor: Balanda Atis, Newark, NJ (US)

(73) Assignee: L'Oreal, Paris (FR)

( * ) Notice: Subject to any disclaimer, the term of this patent is extended or adjusted under 35 U.S.C. 154(b) by 1190 days.

(21) Appl. No.: 11/585,225

(22) Filed: Oct. 24, 2006

(65) Prior Publication Data

US 2008/0095730 A1    Apr. 24, 2008

(51) Int. Cl.
*A61Q 1/10* (2006.01)

(52) U.S. Cl.
USPC ........................................ 424/70.7

(58) Field of Classification Search
None
See application file for complete search history.

(56) References Cited

U.S. PATENT DOCUMENTS

| | | | |
|---|---|---|---|
| 6,607,737 B2 | 8/2003 | Bekele et al. | |
| 6,716,420 B2 * | 4/2004 | Feng et al. | 424/70.7 |
| 6,869,594 B2 * | 3/2005 | Ferrari | 424/70.17 |
| 6,881,400 B2 * | 4/2005 | Collin | 424/70.7 |
| 6,958,155 B2 | 10/2005 | Lu et al. | |
| 7,008,619 B2 * | 3/2006 | Kanji | 424/70.7 |
| 2001/0031280 A1 | 10/2001 | Ferrari et al. | |
| 2002/0107314 A1 | 8/2002 | Pinzon et al. | |
| 2002/0111330 A1 | 8/2002 | Pinzon et al. | |
| 2002/0114773 A1 | 8/2002 | Kanji et al. | |
| 2002/0120036 A1 | 8/2002 | Pinzon et al. | |
| 2002/0122781 A1 | 9/2002 | Pinzon et al. | |
| 2002/0168335 A1 | 11/2002 | Collin | |
| 2003/0147837 A1 | 8/2003 | Cavazzuti et al. | |
| 2003/0161807 A1 | 8/2003 | Lemann | |
| 2003/0185780 A1 | 10/2003 | Ferrari et al. | |
| 2004/0028636 A1 | 2/2004 | Collin | |
| 2004/0042980 A1 | 3/2004 | Kanji et al. | |
| 2004/0091510 A1 | 5/2004 | Feng et al. | |
| 2004/0126401 A1 | 7/2004 | Collin | |
| 2004/0166133 A1 | 8/2004 | Cavazzuti et al. | |
| 2004/0223987 A1 | 11/2004 | Ferrari | |
| 2004/0247549 A1 | 12/2004 | Lu et al. | |
| 2005/0008598 A1 | 1/2005 | Lu et al. | |
| 2005/0008599 A1 | 1/2005 | Lu et al. | |
| 2005/0019358 A1 | 1/2005 | Pinzon et al. | |
| 2005/0062418 A1 | 3/2005 | Kang et al. | |
| 2005/0065251 A1 | 3/2005 | Candau et al. | |
| 2005/0089491 A1 | 4/2005 | Collin | |
| 2005/0089505 A1 | 4/2005 | Collin | |
| 2005/0093850 A1 | 5/2005 | Mori et al. | |
| 2005/0191327 A1 | 9/2005 | Yu et al. | |
| 2005/0287102 A1 | 12/2005 | Ferrari et al. | |

FOREIGN PATENT DOCUMENTS

WO    WO 2004/066918 A2    8/2004

OTHER PUBLICATIONS

Office Action issued Apr. 30, 2012 in Korean Application No. 2009-7008296 (With English Translation).
Japanese Office Action issued Jan. 24, 2012 in patent application No. 2009-534735 with English translation.

* cited by examiner

*Primary Examiner* — Jyothsna Venkat
(74) *Attorney, Agent, or Firm* — Oblon, Spivak, McClelland, Maier & Neustadt, L.L.P.

(57) ABSTRACT

The invention relates to compositions for keratin materials (hair or eyelashes) such as mascaras, topcoats and basecoats containing (a) at least one phosphate surfactant; and (b) at least one polyamide resin.

3 Claims, No Drawings

VOLUMIZING COMPOSITIONS

FIELD OF THE INVENTION

The present invention generally relates to compositions for keratin materials (hair or eyelashes) such as, for example, mascaras, topcoats and basecoats comprising at least one polyamide resin and at least one phosphate surfactant. Such compositions, when applied to keratin materials, impart synergistically improved volume to the keratin materials. Such compositions can also possess improved properties and characteristics such as, for example, increased length of the keratin material, improved transfer-resistance of the composition, improved waterproofing characteristics and/or improved long-wear properties.

BACKGROUND OF THE INVENTION

Many mascaras and other cosmetic compositions have been developed for improved wear, transfer-resistance, and length/volume properties. Such properties are typically accomplished by the use of ingredients that form a film after application. Such compositions generally contain volatile solvents, which evaporate on contact with the skin or eyelashes, leaving behind a layer comprising waxes and/or resins, pigments, fillers, and actives. However, there remains a need for improved cosmetic compositions, particularly mascaras, which possess significantly improved cosmetic properties, particularly one or more of the properties mentioned above.

Accordingly, one aspect of the present invention is a makeup, care and/or treatment composition for keratin materials such as hair or eyelashes which is able to provide significantly improved cosmetic properties to the keratin materials.

SUMMARY OF THE INVENTION

The present invention relates to compositions for keratin materials (hair or eyelashes) such as mascaras, topcoats and basecoats comprising (a) at least one phosphate surfactant; and (b) at least one polyamide resin.

The present invention also relates to methods of increasing the volume and/or length of keratin materials (hair or eyelashes) comprising applying to the keratin material a keratin material volume- and/or length-increasing effective amount of a composition comprising (a) at least one phosphate surfactant; and (b) at least one polyamide resin.

The present invention further relates to methods of making-up keratin materials (hair or eyelashes) comprising applying a keratin material making-up effective amount of a composition comprising (a) at least one phosphate surfactant; and (b) at least one polyamide resin to keratin materials in need of such making-up.

The present invention also relates to methods of treating or caring for keratin materials (hair or eyelashes) by applying compositions of the present invention to the keratin materials in an amount sufficient to treat and/or care for the keratin materials.

The present invention further relates to methods of enhancing the appearance of keratin materials (hair or eyelashes) by applying compositions of the present invention to the keratin materials in an amount sufficient to enhance the appearance of the keratin materials.

It is to be understood that both the foregoing general description and the following detailed description are exemplary and explanatory only, and are not restrictive of the invention.

DETAILED DESCRIPTION OF THE INVENTION

As used herein, the expression "at least one" means one or more and thus includes individual components as well as mixtures/combinations.

"Transfer resistance" as used herein refers to the quality exhibited by compositions that are not readily removed by contact with another material, such as, for example, a glass, an item of clothing or the skin, for example, when eating or drinking. Transfer resistance may be evaluated by any method known in the art for evaluating such. For example, transfer resistance of a composition may be evaluated by a modified "kiss" test. The modified "kiss" test may involve application of the composition to human eyelashes followed by "kissing" or rubbing a material with the eyelashes, for example, a sheet of paper, after expiration of a certain amount of time following application, such as 2 minutes after application. Similarly, transfer resistance of a composition may be evaluated by the amount of product transferred from a wearer to any other substrate, such as transfer from the eyelashes of an individual to clothing after the expiration of a certain amount of time following application. The amount of composition transferred to the substrate (e.g., clothing or paper) may then be evaluated and compared. For example, a composition may be transfer resistant if a majority of the product is left on the eyelashes. Further, the amount transferred may be compared with that transferred by other compositions, such as commercially available compositions.

"Long wear" compositions as used herein, refers to compositions where at least one property chosen from consistency, texture, and color remains the same as at the time of application, as viewed by the naked eye, after an extended period of time, such as, for example, 1 hour, 2 hours, and further such as 8 hours. Long wear properties may be evaluated by any method known in the art for evaluating such properties. For example, long wear may be evaluated by a test involving the application of a composition to eyelashes and evaluating the consistency, texture and color of the composition after an extended period of time. For example, the consistency, texture and color of a mascara composition may be evaluated immediately following application and these characteristics may then be re-evaluated and compared after an individual has worn the mascara composition for a certain amount of time. Further, these characteristics may be evaluated with respect to other compositions, such as commercially available compositions.

"Waterproof" as used herein refers to the ability to repel water and permanence with respect to water. Waterproof properties may be evaluated by any method known in the art for evaluating such properties. For example, a mascara composition may be applied to false eyelashes, which may then be placed in water for a certain amount of time, such as, for example, 20 minutes. Upon expiration of the pre-ascertained amount of time, the false eyelashes may be removed from the water and passed over a material, such as, for example, a sheet of paper. The extent of residue left on the material may then be evaluated and compared with other compositions, such as, for example, commercially available compositions. Similarly, for example, a composition may be applied to skin, and the skin may be submerged in water for a certain amount of time. The amount of composition remaining on the skin after the pre-ascertained amount of time may then be evaluated and compared. For example, a composition may be waterproof if a majority of the product is left on the wearer, e.g., eyelashes.

"Tackiness" as used herein refers to the adhesion between two substances. For example, the more tackiness there is between two substances, the more adhesion there is between the substances. To quantify "tackiness," it is useful to determine the "work of adhesion" as defined by IUPAC associated with the two substances. Generally speaking, the work of adhesion measures the amount of work necessary to separate two substances. Thus, the greater the work of adhesion associated with two substances, the greater the adhesion there is between the substances, meaning the greater the tackiness is between the two substances.

Work of adhesion and, thus, tackiness, can be quantified using acceptable techniques and methods generally used to measure adhesion, and is typically reported in units of force time (for example, gram seconds ("g s")). For example, the TA-XT2 from Stable Micro Systems, Ltd. can be used to determine adhesion following the procedures set forth in the TA-XT2 Application Study (ref: MATI/PO.25), revised January 2000, the entire contents of which are hereby incorporated by reference. According to this method, desirable values for work of adhesion for substantially non-tacky substances include less than about 0.5 g s, less than about 0.4 g s, less than about 0.3 g s and less than about 0.2 g s. As known in the art, other similar methods can be used on other similar analytical devices to determine adhesion.

The cosmetic compositions and methods of the present invention can comprise, consist of, or consist essentially of the essential elements and limitations of the invention described herein, as well as any additional or optional ingredients, components, or limitations described herein or any otherwise useful ingredient found in personal care compositions intended for application to keratin materials.

The composition of the present invention may be in any form suitable for use on eyelashes such as, for example, non-solid anhydrous, oil-free or emulsion compositions (for example, water-in-oil emulsion, oil-in-water emulsion, multiple emulsion (W/O/W or O/W/O), nanoemulsions, etc.). The compositions of the present invention can be mascaras. Generally speaking, mascaras contain colorants such as pigments. Additionally, the compositions of the present invention can be clear or transparent: that is, they can contain little or no colorants. The compositions of the present invention, particularly those with little or no colorants, can be used as a basecoat and/or topcoat for application beneath and/or onto other products applied to eyelashes.

As defined herein, stability is tested by placing the composition in a controlled environment chamber for 8 weeks at 25° C. In this test, the physical condition of the sample is inspected as it is placed in the chamber. The sample is then inspected again at 24 hours, 3 days, 1 week, 2 weeks, 4 weeks and 8 weeks. At each inspection, the sample is examined for abnormalities in the composition such as phase separation if the composition is in the form of an emulsion. The stability is further tested by repeating the 8-week test at 40° C., 37° C., 45° C., 50° C. and/or under freeze-thaw conditions. A composition is considered to lack stability if in any of these tests an abnormality that impedes functioning of the composition is observed. The skilled artisan will readily recognize an abnormality that impedes functioning of a composition based on the intended application.

Phosphate Surfactant

According to the present invention, compositions for keratin materials such as eyelashes or hair comprising at least one phosphate surfactant are provided. Preferably, the at least one phosphate surfactant is selected from monoalkyl phosphates, dialkyl phosphates, salts of monoalkyl phosphates, salts of dialkyl phosphates, and mixtures thereof. More preferably, the monoalkyl phosphates and dialkyl phosphates comprise one or more linear or branched and aliphatic and/or aromatic alkyl chains having from 8 to 22 carbon atoms. According to preferred embodiments, the phosphate surfactant(s) can be neutralized with organic or inorganic bases such as, for example, potassium hydroxide, sodium hydroxide, triethanolamine, arginine, lysine and N-methylglucamine to form the aforementioned salts.

Suitable examples of phosphate surfactants include, but are not limited to, monolauryl phosphate, such as the product sold under the name MAP 20® by Kao Chemicals, the potassium salt of dodecyl phosphate, such as the mixture of mono- and diester (predominantly diester) sold under the name Crafol AP-31® by Cognis, the octyl monoester and the octyl diester of phosphoric acid, such as the mixture sold under the name Crafol AP-20® by Cognis, the ethoxylated (7 mol. of EO) 2-butyloctanol monoester and the ethoxylated (7 mol. of EO) 2-butyloctanol diester of phosphoric acid, such as the mixture sold under the name Isofol 12 7 EO-Phosphate Ester® by Condea, the potassium or triethanolamine salts of monoalkyl ($C_{12}$-$C_{13}$) phosphate, such as the product sold under the references Arlatone MAP 230K-40® and Arlatone MAP 230T-60® by Uniqema, potassium lauryl phosphate, such as the product as a 40% aqueous solution sold under the name Dermalcare MAP XC99/09® by Rhodia Chimie, potassium cetyl phosphate, such as the product sold under the name Arlatone MAP 160K® by Uniqema, and the mixtures of these surfactants.

Preferably, the amount of phosphate surfactant(s) present in the composition ranges from about 1% to 50% by weight of active material with respect to the total weight of the composition, more preferably from about 1.5% to about 40%, more preferably from about 2% to about 30%, and most preferably from about 3% to about 20% by weight of active material with respect to the total weight of the composition, including all ranges and subranges therebetween.

Polyamide Resin

According to the present invention, compositions for keratin materials such as eyelashes or hair comprising at least one polyamide resin are provided. Preferably, the polyamide resin is a polymer of formula (I):

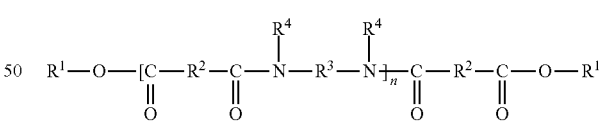

(I)

in which n denotes a number of amide units such that the number of ester groups represents from 10% to 50% of the total number of ester and amide groups; $R^1$ is, independently in each case, an alkyl or alkenyl group containing at least 4 carbon atoms and in particular from 4 to 24 carbon atoms; $R^2$ represents, independently in each case, a $C_4$ to $C_{42}$ hydrocarbon-based group, on condition that 50% of the groups $R^2$ represent a $C_{30}$ to $C_{42}$ hydrocarbon-based group; $R^3$ represents, independently in each case, an organic group containing at least 2 carbon atoms, hydrogen atoms and optionally one or more oxygen or nitrogen atoms; and $R^4$ represents, independently in each case, a hydrogen atom, a $C_1$ to $C_{10}$ alkyl group or a direct bond to $R^3$ or to another $R^4$, such that the nitrogen atom to which $R^3$ and $R^4$ are both attached forms part of a heterocyclic structure defined by $R^4$—N—$R^3$, with at least 50% of the groups $R^4$ representing a hydrogen atom.

In the particular case of formula (I), the terminal fatty chains that are optionally functionalized for the purposes of the invention are terminal chains linked to the last hetero atom, in this case nitrogen, of the polyamide skeleton.

In particular, the ester groups of formula (I), which form part of the terminal and/or pendent fatty chains for the purposes of the invention, represent from 15% to 40% of the total number of ester and amide groups and better still from 20% to 35%. Furthermore, n is advantageously an integer ranging from 1 to 5 and better still greater than 2. Preferably, $R^1$ is a $C_{12}$ to $C_{22}$ and preferably $C_{16}$ to $C_{22}$ alkyl group. Advantageously, $R^2$ can be a $C_{10}$ to $C_{42}$ hydrocarbon-based (alkylene) group. Preferably, at least 50% and better still at least 75% of the groups $R^2$ are groups containing from 30 to 42 carbon atoms. The other groups $R^2$ are $C_4$ to $C_{18}$ and better still $C_4$ to $C_{12}$ hydrogen-containing groups. Preferably, $R^3$ represents a $C_2$ to $C_{36}$ hydrocarbon-based group or a polyoxyalkylene group and $R^4$ represents a hydrogen atom. Preferably, $R^3$ represents a $C_2$ to $C_{12}$ hydrocarbon-based group.

The hydrocarbon-based groups may be linear, cyclic or branched, and saturated or unsaturated groups. Moreover, the alkyl and alkylene groups may be linear or branched, and saturated or unsaturated groups.

In general, the polymers of formula (I) are in the form of mixtures of polymers, these mixtures also possibly containing a synthetic product corresponding to a compound of formula (I) in which n is 0, i.e. a diester.

Non-limiting examples of the at least one polyamide resin include, but are not limited to, the commercial products under the names Uniclear 80 and Uniclear 100. These are sold, respectively, in the form of an 80% (in terms of active material) gel in a mineral oil and a 100% (in terms of active material) gel. These polymers have a softening point ranging from 88° C. to 94° C., and may be mixtures of copolymers derived from monomers of (i) $C_{36}$ diacids and (ii) ethylenediamine, and have a weight-average molecular mass of about 6000. Terminal ester groups result from esterification of the remaining acid end groups with at least one alcohol chosen from cetyl alcohol and stearyl alcohol. A mixture of cetyl and stearyl alcohols is sometimes called cetylstearyl alcohol. Also, the polyamide resins can be amide terminated, such as Sylvaclear A200, or polyalkyleneoxy terminated, such as Sylvaclear AF1900. Such polyamide resins are available, for instance, from Arizona Chemical Company, Jacksonville, Fla., and are described in US patent application publication no. 2005/0089505, U.S. Pat. No. 5,783,657, U.S. Pat. No. 6,402,408, U.S. Pat. No. 6,268,466, U.S. Pat. No. 6,552,160, the entire contents of which are hereby incorporated by reference.

Other non-limiting examples of the at least one polyamide resin which may be used in the composition according to the present invention include polyamide resins resulting from the condensation of at least one aliphatic dicarboxylic acid and at least one diamine, the carbonyl and amine groups being condensed via an amide bond. Examples of these polyamide polymers are those sold under the brand name Versamid by the companies General Mills Inc. and Henkel Corp. (Versamid 930, 744 or 1655) or by the company Olin Mathieson Chemical Corp. under the brand name Onamid, in particular Onamid S or C. These resins have a weight-average molecular mass ranging from 6000 to 9000. For further information regarding these polyamides, reference may be made to U.S. Pat. Nos. 3,645,705 and 3,148,125, the disclosures of which are hereby incorporated by reference.

Other examples of polyamides include those sold by the company Arizona Chemical under the references Uni-Rez (2658, 2931, 2970, 2621, 2613, 2624, 2665, 1554, 2623 and 2662) and the product sold under the reference Macromelt 6212 by the company Henkel. For further information regarding these polyamides, reference may be made to U.S. Pat. No. 5,500,209, the disclosure of which is hereby incorporated by reference. Such polyamides display high melt viscosity characteristics. MACROMELT 6212, for example, has a high melt viscosity at 190° C. of 3040 poise (as measured by a Brookfield Viscometer, Model RVF #3 spindle, 20 RPM).

Also, the at least one polyamide resin may be chosen from polyamide resins from vegetable sources. Polyamide resins from vegetable sources may be chosen from, for example, the polyamide resins of U.S. Pat. Nos. 5,783,657 and 5,998,570, the disclosures of which are herein incorporated by reference.

Preferably, the at least one polyamide resin is present in an amount ranging from about 0.5% to about 80% by weight of active material with respect to the total weight of the composition, more preferably from about 2% to about 60%, more preferably from about 4% to about 40%, and most preferably from about 5% to about 20% by weight of active material with respect to the total weight of the composition, including all ranges and subranges therebetween.

According to the present invention, compositions comprising at least one phosphate surfactant and at least one polyamide resin possess synergistically improved properties with respect to volumizing (that is, thickening) keratin materials such as hair or eyelashes. That is, surprisingly, the combination of phosphate surfactant and polyamide resin results in increased volume (or thickness) of keratin materials such as hair or eyelashes in an amount which is more than additive.

Coloring Agents

According to the present invention, the compositions may optionally comprise at least one coloring agent (colorant). Suitable coloring agents include but are not limited to pigments, dyes, such as liposoluble dyes, nacreous pigments, and pearling agents. Typically, when the composition contains colorants, it is a make-up composition such as a mascara composition. Alternatively, when the composition does not contain colorants, it is a clear or transparent composition which can be used as a basecoat (or topcoat) prior to (or after) application of a make-up composition such as a mascara to eyelashes, or it can be used as a hair treatment composition such as, for example, a hair conditioner or mousse. However, it is possible that topcoats, basecoats, hair treatment products and the like could contain colorants, and/or that a mascara or make-up composition could contain little or no colorant.

Representative liposoluble dyes which may be used according to the present invention include Sudan Red, DC Red 17, DC Green 6, β-carotene, soybean oil, Sudan Brown, DC Yellow 11, DC Violet 2, DC Orange 5, annatto, and quinoline yellow. The liposoluble dyes, when present, generally have a concentration ranging up to 20% by weight of the total weight of the composition, such as from 0.0001% to 6%.

The nacreous pigments which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The nacreous pigments, if present, be present in the composition in a concentration ranging up to 50% by weight of the total weight of the composition, such as from 0.1% to 20%, preferably from 0.1% to 15%.

The pigments, which may be used according to the present invention, may be chosen from white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, strontium, calcium, and aluminum.

If present, the pigments may be present in the composition in a concentration ranging up to 50% by weight of the total weight of the composition, such as from 0.5% to 40%, and further such as from 2% to 30%. In the case of certain products, the pigments, including nacreous pigments, may, for example, represent up to 50% by weight of the composition.

According to particularly preferred embodiments, the compositions of the present invention are in the form of an emulsion. Suitable emulsion forms include but are not limited to oil-in-water, water-in-oil, oil-in-water-in-oil, water-in-oil-in-water and nanoemulsions (emulsions whose oil globules are of very fine particle size, that is to say that they have a number-average size of less than about 100 nanometers (nm)). Emulsions contain at least one oil phase and at least one aqueous phase. Typically speaking, emulsions contain surfactants or surfactant-like materials which provide stability to the emulsions and inhibit de-phasing of the emulsions.

One particularly preferred embodiment of the present invention is a composition for application to keratin materials (hair or eyelashes) which is an emulsion but which is substantially free of TEA-stearate (that is, less than 0.25% of TEA-stearate) or free of TEA Stearate (that is, less than 0.05% TEA-stearate).

Additional Ingredients

The compositions of the present invention can also comprise any additive usually used in the field under consideration. For example, film forming agents, dispersants, antioxidants, essential oils, preserving agents, fragrances, liposoluble polymers that are dispersible in the medium, fillers, neutralizing agents, cosmetic and dermatological active agents such as, for example, emollients, moisturizers, vitamins, anti-wrinkle agents, essential fatty acids, sunscreens, and mixtures thereof can be added. A non-exhaustive listing of such ingredients can be found in U.S. patent application Ser. No. 10/733,467, filed Dec. 12, 2003, the entire contents of which is hereby incorporated by reference. Further examples of suitable additional components can be found in the other references which have been incorporated by reference in this application, including but not limited to the applications from which this application claims priority. Still further examples of such additional ingredients may be found in the *International Cosmetic Ingredient Dictionary and Handbook* ($9^{th}$ ed. 2002).

A person skilled in the art will take care to select the optional additional additives and/or the amount thereof such that the advantageous properties of the composition according to the invention are not, or are not substantially, adversely affected by the envisaged addition.

These substances may be selected variously by the person skilled in the art in order to prepare a composition which has the desired properties, for example, consistency or texture.

These additives may be present in the composition in a proportion from 0% to 99% (such as from 0.01% to 90%) relative to the total weight of the composition and further such as from 0.1% to 50% (if present).

Needless to say, the composition of the invention should be cosmetically or dermatologically acceptable, i.e., it should contain a non-toxic physiologically acceptable medium and should be able to be applied to the eyelashes of human beings.

Specific examples of additional ingredients include oils, particularly if the composition is an anhydrous composition or an emulsion. Any oils can be used in accordance with the present invention. The oils can be volatile or non-volatile, silicone-based and/or hydrocarbon-based, etc. Thus, for example, the external oil phase may contain, independently or in combination, volatile silicone oils, non-volatile silicone oils, volatile non-silicone oils and non-volatile non-silicone oils.

In one embodiment, the compositions of the present invention are substantially free of silicone oils (i.e., contain less than about 1% of silicone oil). In another embodiment, the compositions are substantially free of non-silicone oils (i.e., contain less than about 1% of non-silicone oil). In another embodiment, the compositions are substantially free of non-volatile oils (i.e., contain less than about 1% of non-volatile oil). In yet another embodiment, the compositions are substantially free of volatile oils (i.e., contain less than about 1% of volatile oil).

According to one embodiment, the oil phase may contain one or more volatile silicone oils. Examples of such volatile silicone oils include linear or cyclic silicone oils having a viscosity at room temperature less than or equal to 6cSt and having from 2 to 7 silicone atoms, these silicones being optionally substituted with alkyl or alkoxy groups of 1 to 10 carbon atoms. Suitable oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Non-limiting examples of volatile silicone oils are listed in Table 1 below.

TABLE 1

| Compound | Flash Point (° C.) | Viscosity (cSt) |
| --- | --- | --- |
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane(L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |
| PDMS DC 200 (5 cSt) from Dow Corning | 134 | 5 |
| PDMS DC 200 (3 St) from Dow Corning | 102 | 3 |

Further, a volatile linear silicone oil may be employed in the compositions of the present invention. Suitable volatile linear silicone oils include those described in U.S. Pat. No. 6,338,839 and WO03/042221, the contents of which are incorporated herein by reference. In one embodiment the volatile linear silicone oil is decamethyltetrasiloxane. In another embodiment, the decamethyltetrasiloxane is further combined with another solvent that is more volatile than decamethyltetrasiloxane.

The volatility of the solvents/oils can be determined using the evaporation speed as set forth in U.S. Pat. No. 6,338,839.

Examples of other silicone oils that may be used in the invention include non-volatile linear polydimethylsiloxanes (PDMSs), that are liquid at room temperature; polydimethylsiloxanes comprising alkyl, alkoxy or phenyl groups, which are pendent and/or at the end of a silicone chain, these groups each containing from 2 to 24 carbon atoms; phenylsilicones, for instance phenyl trimethicones, phenyl dimethicones, phenyl trimethylsiloxydiphenylsiloxanes, diphenyl dimethicones, diphenyl methyldiphenyl trisiloxanes and 2-phenylethyl trimethylsiloxysilicates.

According to other preferred embodiments, the oil phase may contain one or more non-silicone volatile oils and may be selected from volatile hydrocarbon oils, alcohols, volatile esters and volatile ethers. Examples of such volatile non-silicone oils include, but are not limited to, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, isohexadecane, and for example, the oils sold under the trade names of Isopar or Permethyl, the $C_8$ to $C_{16}$ branched esters such as isohexyl or isodecyl neopentanoate and their mixtures. Preferably, the volatile non-silicone oils have a flash point of at least 40° C.

TABLE 2

| Compound | Flash Point (° C.) |
|---|---|
| Isododecane | 43 |
| Isohexadecane | 102 |
| Isodecyl Neopentanoate | 118 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

Examples of other non-silicone oils which can be used in the compositions of the present invention include polar oils such as:

hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;

synthetic oils or esters of formula $R_5COOR_6$ in which $R_5$ represents a linear or branched higher fatty acid residue containing from 1 to 40 carbon atoms, including and better still from 7 to 19 carbon atoms, and $R_6$ represents a branched hydrocarbon-based chain containing from 1 to 40 carbon atoms, including and better still from 3 to 20 carbon atoms, with $R_6+R_7 \geq 10$, such as, for example, Purcellin oil (cetostearyl octanoate), isononyl isononanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;

synthetic ethers containing from 10 to 40 carbon atoms; $C_8$ to $C_{26}$ fatty alcohols, for instance oleyl alcohol; and mixtures thereof.

Preferably, the oils, if present, represent from about 5% to about 80% by weight of the total weight of the composition, more preferably from about 10% to about 60% of the total weight of the composition, and most preferably from about 15% to about 50%, including all ranges and subranges therebetween.

Water, when present, preferably represents from about 1% to about 70% by weight of the total weight of the composition, more preferably from about 5% to about 60% of the total weight of the composition, and most preferably from about 10% to about 50%, including all ranges and subranges therebetween.

According to other embodiments of the present invention, the composition may optionally further comprise a film forming or structuring polymer such as, for example, a copolymer comprising at least one styrene block, a hydrocarbon resin, a polyorganosiloxane-containing polymer, and mixtures thereof.

Suitable copolymers comprising at least one styrene block include, but are not limited to, triblock copolymers such as those of the polystyrene/polyisoprene or polystyrene/polybutadiene type, for example those sold or made under the name "Luvitol HSB" by BASF, and those of the polystyrene/copoly (ethylene-propylene) type or alternatively of the polystyrene/copoly(ethylene/butylene) type, such as those sold or made under the brand name "Kraton" by Shell Chemical Co. or Gelled Permethyl 99A by Penreco. Specific examples include Kraton (G1650 (SEBS), Kraton G1651 (SEBS), Kraton G1652 (SEBS), Kraton G1657X (SEBS), Kraton G1701X (SEP), Kraton G1702X (SEP), Kraton G1726X (SEB), Kraton G1750X (EP) multiarm, Kraton G1765X (EP) multiarm, Kraton D-1101 (SBS), Kraton D-1102 (SBS), Kraton D-1107 (SIS), Gelled Permethyl 99A-750, Gelled Permethyl 99A-753-58 (mixture of starburst block polymer and triblock polymer), Gelled Permethyl 99A-753-59 (mixture of starburst block polymer and triblock polymer), Versagel 5970 and Versagel 5960 from Penreco (mixture of starburst polymer and triblock polymer in isododecane), and OS 129880, OS 129881 and OS 84383 from Lubrizol (styrene-methacrylate copolymer). Also, such polymers are described in patent applications WO 98/38981 and US 2002/0055562, the disclosures of which are hereby incorporated by reference.

Suitable hydrocarbon resins include but are not limited to aliphatic hydrocarbon resins, hydrogenated aliphatic hydrocarbon resins, aliphatic/aromatic hydrocarbon resins, hydrogenated aliphatic aromatic hydrocarbon resins, cycloaliphatic hydrocarbon resins, hydrogenated cycloaliphatic resins, cycloaliphatic/aromatic hydrocarbon resins, hydrogenated cycloaliphatic/aromatic hydrocarbon resins, aromatic hydrocarbon resins, hydrogenated aromatic hydrocarbon resins, polyterpene resins, terpene-phenol resins, rosins, rosin esters, resins grafted with an unsaturated acid or anhydride, and mixtures of any two or more thereof. When referring to hydrogenated resins, hydrogenated includes resins that are at least partially hydrogenated and substantially hydrogenated.

Examples of suitable hydrocarbon resins include but are note limited to ESCOREZ™ 1310 and EMPR™ 118 available from ExxonMobil Chemical Company, Houston, Tex., PICCOTAC™ 1020, 1020E, and 9095 available from Eastman Chemical Company, Kingsport, Term., WINGTACK™

10, 86, PLUS, and 95 available from Goodyear Chemical Company, and QUINTONE™ K100, R100, and M100 available from Nippon Zeon of Japan.

Other suitable hydrocarbon resins are disclosed in U.S. patent application publication no. 2004/0092648, published May 13, 2004, the entire contents of which is hereby incorporated by reference.

Suitable hydrocarbon resins further include low molecular weight, lightly colored, inert thermoplastic resins derived from petrochemical feedstocks. Preferably, these thermoplastic polymers are also partially or fully hydrogenated. These include certain hydrogenated polycyclopentadienes and hydrogenated styrene/methylstyrene/indene copolymers sold under the trade name REGALITE. Some of the REGALITES are made from $C_{8+}$ monomers which include, without limitation, vinyl toluene, dicyclopentadiene, indene, alpha-methyl styrene, styrene and methyl indene. These low molecular weight hydrocarbon resins may be found in a number of commercial products including without limitation those sold by Eastman Chemical Middelburg BV, Tobias Asserlaan 5, 2517 KC Den Haag, the Netherlands, under the trademark REGALITE, PICCOTAC and EASTOTAC. A material that typifies a hydrocarbon resin that may be used in accordance with the present invention is REGALITE®R1090 hydrogenated thermoplastic resin, as described in product data sheet 65.014-E3, dated February, 2001. Other useful polyolefins of this type include REGALITE®R1125, R1100 and R9100.

Suitable polyorganosiloxane-containing polymers can generally be described as polymers chosen from homopolymers and copolymers, preferably, with a weight-average molecular mass ranging from about 500 to about $2.5 \times 10^6$ or more, comprising at least one moiety comprising: at least one polyorganosiloxane group comprising, preferably, from 1 to about 10,000 organosiloxane units in the chain of the moiety or in the form of a graft, and at least two groups capable of establishing hydrogen interactions. Examples of suitable polyorganosiloxane-containing polymers can be found in U.S. patent application Ser. No. 11/254,919, filed Oct. 21, 2005, the entire contents of which is hereby incorporated by reference.

More specifically, preferred polyorganosiloxane-containing polymers comprise at least one moiety chosen from formulae (III) and (IV):

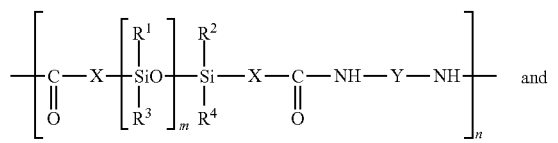

(III)

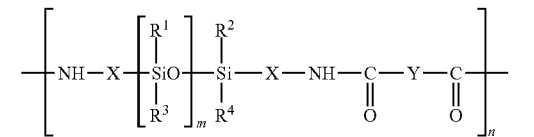

(IV)

in which:
1) $R^1$, $R^2$, $R^3$ and $R^4$, which may be identical or different, are chosen from:
   linear, branched and cyclic, saturated and unsaturated, $C_1$ to $C_{40}$ hydrocarbon-based groups, optionally comprising in the chain at least one atom chosen from oxygen, sulphur and nitrogen, and also optionally being partially or totally substituted with at least one fluorine atom,
   $C_6$ to $C_{10}$ aryl groups, optionally substituted with at least one $C_1$ to $C_4$ alkyl group,
   polyorganosiloxane chains optionally comprising at least one atom chosen from oxygen, sulphur and nitrogen;
2) the groups X, which may be identical or different, are chosen from linear and branched $C_1$ to $C_{30}$ alkylenediyl groups, optionally comprising in the chain at least one atom chosen from oxygen and nitrogen;
3) Y is chosen from saturated and unsaturated, $C_1$ to $C_{50}$ linear and branched divalent alkylene, arylene, cycloalkylene, alkylarylene and arylalkylene groups, optionally comprising at least one atom chosen from oxygen, sulphur and nitrogen, and optionally substituted by one of the following atoms and groups of atoms:
   fluorine, hydroxyl, $C_3$ to $C_8$ cycloalkyl, $C_1$ to $C_{40}$ alkyl, $C_5$ to $C_{10}$ aryl, phenyl optionally substituted with 1 to 3 $C_1$ to $C_3$ alkyl groups, $C_1$ to $C_3$ hydroxyalkyl and $C_1$ to $C_6$ aminoalkyl, or
4) Y represents a group corresponding to the formula:

in which
   T is chosen from linear and branched, saturated and unsaturated, $C_3$ to $C_{24}$ trivalent and tetravalent hydrocarbon-based groups optionally substituted with a polyorganosiloxane chain, and optionally comprising at least one atom chosen from O, N and S, or T represents a trivalent atom chosen from N, P and Al, and
   $R^5$ is chosen from linear and branched $C_1$ to $C_{50}$ alkyl groups and polyorganosiloxane chains, optionally comprising at least one group chosen from ester, amide, urethane, thiocarbamate, urea, thiourea and sulphonamide groups, which may optionally be linked to another chain of the polymer;
5) n is an integer ranging from 2 to 500, and m is an integer ranging from 1 to 1 000.

Particularly preferred polyorganosiloxane-containing polymers are polysiloxane-polyamide copolymers available from Dow Corning such as, for example, Nylon-611/Dimethicone copolymer.

According to preferred embodiments of the present invention, methods of increasing keratin material (hair or eyelash) volume and/or length comprising applying to keratin materials a keratin material volume- and/or length-increasing effective amount of a composition comprising (a) at least one phosphate surfactant; and (b) at least one polyamide resin are provided. The compositions may be applied to the keratin materials as needed, preferably once or twice daily, more preferably once daily and then preferably allowed to dry before subjecting to contact such as with clothing or other objects.

According to particularly preferred embodiments, sufficient phosphate surfactant is combined with sufficient polyamide resin such that the performance properties of the compositions are greater than the performance properties of compositions containing either ingredient individually (that is, synergism exists with respect to the phosphate surfactant and the polyamide resin).

According to yet further embodiments of the present invention, methods of making-up keratin materials (hair or eyelashes) comprising applying a keratin material making-up effective amount of a composition comprising (a) at least one phosphate surfactant; and (b) at least one polyamide resin to keratin materials in need of such making-up are provided.

According to preferred embodiments of the present invention, methods of treating or caring for keratin materials (hair or eyelashes) by applying compositions of the present invention to the keratin materials in an amount sufficient to treat and/or care for the keratin materials are provided.

According to other preferred embodiments, methods of enhancing the appearance of keratin materials (hair or eyelashes) by applying compositions of the present invention to the keratin materials in an amount sufficient to enhance the appearance of the keratin materials are provided.

In accordance with the preceding preferred embodiments, the compositions of the present invention are applied topically to keratin materials (hair or eyelashes) in an amount sufficient to treat, care for and/or make up the keratin materials, or to enhance the appearance of the keratin materials. The compositions may be applied to eyelashes as needed, preferably once or twice daily, more preferably once daily and then preferably allowed to dry before subjecting to contact such as with clothing or other objects.

The present invention also envisages kits and/or prepackaged materials suitable for consumer use containing one or more compositions according to the description herein (for example, kits containing (1) a mascara; and (2) a basecoat and/or topcoat). The packaging and application device for any subject of the invention may be chosen and manufactured by persons skilled in the art on the basis of their general knowledge, and adapted according to the nature of the composition to be packaged. Indeed, the type of device to be used can be in particular linked to the consistency of the composition, in particular to its viscosity; it can also depend on the nature of the constituents present in the composition, such as the presence of volatile compounds.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLE 1

Preparation of Compositions

| Phase | INCI Name | Example A | Example B | Example C |
|---|---|---|---|---|
| A | DI Water | 43.10 | 47.10 | 48.60 |
|  | Hydroxypropylcellulose | 0.20 | 0.20 | 0.20 |
|  | PVP K90 | 1.00 | 1.00 | 1.00 |
|  | Pentylene Glycol | 2.00 | 2.00 | 2.00 |
|  | Methylparaben | 0.35 | 0.35 | 0.35 |
|  | TEA | N/A | N/A | N/A |
|  | Di Sodium EDTA | 0.10 | 0.10 | 0.10 |
|  | 50% Sodium Hydroxide Solution | 1.00 | 1.00 | 1.00 |
| B | Beeswax | 4.00 | 4.00 | 4.00 |
|  | Paraffin | 3.00 | 3.00 | 3.00 |
|  | Carnauba Wax | 4.00 | 4.00 | 4.00 |
|  | Propylparaben | 0.05 | 0.05 | 0.05 |
|  | Polyamide Resin (Uniclear) | 8.50 | N/A | N/A |
|  | Ganex V220 | 4.00 | 4.00 | 4.00 |
|  | Lexorez 200 | 5.00 | 5.00 | 5.00 |
|  | Polyisobutene | 1.00 | 1.00 | 1.00 |
|  | Black Iron Oxide | 5.50 | 5.50 | 5.50 |
|  | Arlatone MAP 160K | 6.00 | 6.00 | 6.00 |
|  | Regalite R1100 | N/A | N/A | 2.00 |
|  | Kraton G1657 | N/A | N/A | 1.00 |
|  | Nylon-611/Dimethicone copolymer | N/A | 4.50 | N/A |
| C | Simethicone | 0.10 | 0.10 | 0.10 |
| E | Ultrasol | 10.00 | 10.00 | 10.00 |
| F | Liquapar Optima | 1.10 | 1.10 | 1.10 |
|  |  | 100.00 | 100.00 | 100.00 |

| Phase | INCI Name | Example D | Example E |
|---|---|---|---|
| A | DI Water | 42.60 | 35.60 |
|  | Hydroxypropylcellulose | 0.20 | 0.20 |
|  | PVP K90 | 1.00 | 1.00 |
|  | Pentylene Glycol | 2.00 | 2.00 |
|  | Methylparaben | 0.35 | 0.35 |
|  | Di Sodium EDTA | 0.10 | 0.10 |
|  | 50% Sodium Hydroxide Solution | 1.00 | 1.00 |
| B | Beeswax | 4.00 | 4.00 |
|  | Paraffin | 3.00 | 3.00 |
|  | Carnauba Wax | 4.00 | 4.00 |
|  | Propylparaben | 0.05 | 0.05 |
|  | Polyamide Resin (Uniclear) | N/A | 8.50 |
|  | Ganex V220 | 4.00 | 4.00 |
|  | Lexorez 200 | 5.00 | 5.00 |
|  | Polyisobutene | 1.00 | 1.00 |
|  | Black Iron Oxide | 5.50 | 5.50 |
|  | Arlatone MAP 160K | 6.00 | 6.00 |
|  | Regalite R1100 | 8.00 | 2.00 |
|  | Kraton G1657 | 1.00 | 1.00 |
|  | Nylon-611/Dimethicone copolymer | N/A | 4.50 |
| C | Simethicone | 0.10 | 0.10 |
| E | Ultrasol | 10.00 | 10.00 |
| F | Liquapar Optima | 1.10 | 1.10 |
|  |  | 100.00 | 100.00 |

| Phase | INCI Name | Example F |
|---|---|---|
| A | DI Water | 35.60 |
|  | Hydroxypropylcellulose | 0.20 |
|  | PVP K90 | 1.00 |
|  | Pentylene Glycol | 2.00 |
|  | Methylparaben | 0.35 |
|  | Di Sodium EDTA | 0.10 |
|  | 50% Sodium Hydroxide Solution | 1.00 |
| B | Beeswax | 8.00 |
|  | Paraffin | 7.00 |
|  | Carnauba Wax | 7.00 |
|  | Propylparaben | 0.05 |
|  | Polyamide Resin (Uniclear) | n/a |
|  | Ganex V220 | 7.00 |
|  | Lexorez 200 | 7.00 |
|  | Polyisobutene | 1.00 |

-continued

| Phase | | | |
|---|---|---|---|
| | Black Iron Oxide | 5.50 | |
| | Arlatone MAP 160K | 6.00 | |
| C | Simethicone | 0.10 | |
| E | Ultrasol | 10.00 | |
| F | Liquapar Optima | 1.10 | |
| | | 100.00 | |

| Phase | INCI Name | Example G |
|---|---|---|
| A | DI Water | 41.50 |
| | Hydroxypropylcellulose | 0.20 |
| | PVP K90 | 1.00 |
| | Pentylene Glycol | 2.00 |
| | Methylparaben | 0.35 |
| | TEA | 1.60 |
| | Di Sodium EDTA | 0.10 |
| | 50% Sodium Hydroxide Solution | 1.00 |
| B | Beeswax | 4.00 |
| | Paraffin | 3.00 |
| | Carnauba Wax | 4.00 |
| | Propylparaben | 0.05 |
| | Polyamide Resin (Uniclear) | 8.50 |
| | Ganex V220 | 4.00 |
| | Lexorez 200 | 5.00 |
| | Polyisobutene | 1.00 |
| | Black Iron Oxide | 5.50 |
| | Stearic Acid | 3.00 |
| | Glyceryl Stearate | 3.00 |
| C | Simethicone | 0.10 |
| E | Ultrasol | 10.00 |
| F | Liquapar Optima | 1.10 |
| | TOTAL | 100.00 |

EXAMPLE 2

Determination of Volumizing Properties

The volumizing properties of the identified compositions were analyzed as follows. The identified compositions were applied to lash sets (five fibers on a support) 15 times using a mascara brush loaded with each composition. The width of each of the fibers was determined using a digital video camera (and commercially available image analysis software from ImagePro to convert the digital image to a numerical figure) at the midpoint of each fiber (1) before application of the identified compositions; and (2) after application of the identified compositions 15 times. The average value of the five fibers was determined for each lash set. The average value of the lash set after application of the identified composition was then compared to the average value of the lash set prior to application of the identified composition for each composition tested. The difference between these average values represented the % increase in lash volume resulting from application of the identified compositions. The results of this analysis are set forth below.

| Product | Width Differences = Avg. Post Treated − Avg. Pre Treated | % Volume Increase |
|---|---|---|
| Example E (Phosphate Surfactant, Polyamide Resin) | 0.156 | 1151 |
| Example A (Phosphate Surfactant, Polyamide Resin) | 0.148 | 1102 |
| Example F (Phosphate Surfactant, no Polyamide Resin) | 0.125 | 468 |
| Example G (Polyamide Resin, no Phosphate Surfactant) | 0.094 | 337 |
| Example C (Phosphate Surfactant, no Polyamide Resin) | 0.067 | 319 |
| Example B (Phosphate Surfactant, no Polyamide Resin) | 0.055 | 235 |
| Example D (Phosphate Surfactant, no Polyamide Resin) | 0.032 | 100 |

What is claimed is:

1. A method of increasing eyelash volume or length comprising applying to eyelashes a mascara composition comprising:

at least one coloring agent;

a phosphate surfactant selected from the group consisting of potassium cetyl phosphate, potassium lauryl phosphate, and potassium dodecyl phosphate; and ethylenediamine/stearyl dimer dilinoleate copolymer;

wherein the phosphate surfactant(s) and the ethylenediamine/stearyl dimer dilinoleate copolymer are present in a synergistic eyelash volumizing effective amount.

2. The method according to claim 1, wherein the mascara composition is in the form of an emulsion.

3. The method according to claim 1, further comprising nylon 611/dimethicone polymer.

* * * * *